United States Patent [19]

Mollenauer et al.

[11] Patent Number: 5,709,692
[45] Date of Patent: Jan. 20, 1998

[54] SURGICAL INSTRUMENT FOR PLACING SUTURE OR FASTENERS

[75] Inventors: Kenneth H. Mollenauer, Santa Clara; Michelle Y. Monfort, Los Gatos, both of Calif.

[73] Assignee: General Surgical Innovations, Cupertino, Calif.

[21] Appl. No.: 727,196

[22] Filed: Oct. 8, 1996

Related U.S. Application Data

[62] Division of Ser. No. 307,188, Sep. 16, 1994, Pat. No. 5,562,685.

[51] Int. Cl.$^6$ ........................................ A61B 17/00
[52] U.S. Cl. ........................... 606/141; 606/139; 606/222; 112/169
[58] Field of Search ........................ 606/222–227, 606/139, 144, 147, 148; 112/169, 80.03; 223/102, 104

[56] References Cited

U.S. PATENT DOCUMENTS

| 3,123,077 | 3/1964 | Alcamo | 606/228 |
| 4,204,541 | 5/1980 | Kapitanov | 606/139 |
| 4,641,652 | 2/1987 | Hutterer et al. | 606/139 |
| 5,281,236 | 1/1994 | Bagnato et al. | 606/139 |
| 5,501,692 | 3/1996 | Riza | 606/139 |

FOREIGN PATENT DOCUMENTS

| 404226643 | 8/1992 | Japan | 606/222 |

*Primary Examiner*—Jeffrey A. Schmidt
*Attorney, Agent, or Firm*—Howell & Haferkamp

[57] ABSTRACT

A surgical instrument for use in placing suture or fasteners in tissue at a remote location such as a laproscopic surgery is comprised of an elongated handle having a coiled projection at its distal end. The coiled projection is employed in penetrating and positioning a length of suture or fastener in tissue, for example, as in tissue proximation.

14 Claims, 4 Drawing Sheets

SURGICAL INSTRUMENT FOR PLACING SUTURE OR FASTENERS

This is a divisional application Ser. No. 08/307,188 filed on Sep. 16, 1994 now U.S. Pat. No. 5,562,685.

BACKGROUND OF THE INVENTION

(1) Field of the Invention

The present invention pertains to a surgical instrument employed in suturing tissue at a remote location such as in laparoscopic surgery.

(2) Description of the Related Art

Various different types of surgical instruments are known in the prior art for use in suturing body tissue. Many of these prior art instruments have been developed with the intent to facilitate passing a length of suture through body tissue and then tying a knot in the suture material at surgical sites located in remote areas that are difficult to access. Many prior art instruments are designed for use in surgical procedures where large, deep incisions are made into the body. The instruments enable suturing at remote locations in these deep body incisions. Many prior art instruments are also designed for use in laparoscopic surgical procedures where small incisions are made and the remote surgical site is accessed through cannulas or tubes. Examples of known instruments employed in tying knots in lengths of suture material are disclosed in the Larzelere U.S. Pat. No. 2,595,086, Mulhollan et al. U.S. Pat. No. 4,602,635, Hutterer et al. U.S. Pat. No. 4,641,652, Hayhurst U.S. Pat. No. 4,961,741, Li U.S. Pat. No. 5,084,058, Li U.S. Pat. No. 5,087,263, Li U.S. Pat. No. 5,163,946, Li U.S. Pat. No. 5,133,723, Mayzels et al. U.S. Pat. No. 5,269,791 and Bagnato et al. U.S. Pat. No. 5,281,236. Examples of known instruments employed in passing suture material through body tissue at a remote location are disclosed in the Fukuda U.S. Pat. No. 4,345,601, Wilk et al. U.S. Pat. No. 5,037,433 and Snyder U.S. Pat. No. 5,250,053.

Common characteristics of many known surgical suturing instruments are that they are very complicated to operate, often requiring the use of several instruments together when employed in laparoscopic surgery and are therefore often time consuming to set up and use.

SUMMARY OF THE INVENTION

The present invention overcomes disadvantages commonly associated with prior art surgical suturing instruments by providing a simplified surgical instrument for passing a length of suture or a fastener through body tissue in suturing the tissue. More specifically, the surgical instrument of the present invention may be employed in either open incision or laparoscopic surgery procedures to position a length of suture material proximate to a surgical location and to form one or more passes of the suture material through the body tissue to be sutured with the single instrument of the invention, and in certain embodiments through the use of a single surgical grasper with the instrument of the invention.

The suturing instrument of the present invention is provided in several embodiments. Each of the embodiments employs an elongated handle having opposite distal and proximal ends that is held and manipulated by a surgeon at its proximal end in use of the instrument of the invention in deep incision surgery and in laparoscopic surgery. A coiled projection having at least one helical revolution formed therein projects from the distal end of the handle. The distal end of the coiled projection has a pointed tip enabling penetration of this end of the coil through body tissue.

In a first embodiment of the apparatus, the handle is hollow and communicates with a hollow interior bore that extends through the coil and exits the coil through a bore opening at the pointed distal end of the coil. A length of flexible filament extends through the coil and the hollow handle. A distal end of the filament adjacent the bore opening of the coil has a loop formed therein. The opposite proximal end of the filament is connected to a mechanism in the handle that is reciprocated in the handle in response to manual reciprocating manipulation of a knob on the exterior of the handle. Manual reciprocation of the knob between first and second positions relative to the handle selectively projects the filament loop from the bore opening at the distal end of the coil and retracts the filament loop back into the core interior bore through the bore opening.

In use, the filament loop is extended from the coil bore and a length of suture is inserted through the loop. The loop is then retracted back into the bore thereby securing the length of suture to the tip of the instrument coil. The tip of the coil may then be passed through the body tissue to be sutured, simultaneously pulling the length of suture through the penetration of the body tissue with the length of suture draped against the exterior of the coil as the coil is pushed through the tissue penetration. The loop is then extended and the suture removed from the loop prior to the coil of the instrument being retracted through the penetration leaving the length of suture in the penetration. Alternatively, the pointed tip of the instrument coil may first be penetrated through the tissue to be sutured and then the loop extended from the tip. A length of suture is then inserted through the loop and the loop is retracted into the coil interior bore. The coil is then retracted through the penetration simultaneously pulling the length of suture through the penetration. Once removed from the penetration, the loop is extended and the length of suture is removed from the loop.

The second embodiment of the inventive apparatus is similar to the first described embodiment except that it does not employ the length of filament with the loop at its distal end but instead employs a fastener inserted into the open bore at the distal end of the coil. The fastener has a pointed tip that projects from the bore opening and enables the bore distal end to be penetrated through body tissue. One or more barbs on the fastener tip prevent its retraction from the tissue penetration. A proximal end of the fastener received in the bore interior also has several barbs formed thereon. In use, the pointed tip of the fastener is driven by the coil of the instrument through the body tissue into the desired position. The tip may pass through more than one tissue segment if proximation of the tissue segments is the objective. The coil is then retracted back through the penetration with the barbs at the pointed tip of the fastener and the barbs at the proximal end of the fastener holding the fastener in the penetration through the tissue thereby suturing the tissue. Other fastener end features, such as an eye for receiving suture, may be employed.

The third embodiment of the instrument again is similar to the first described embodiment except that it does not employ the length of filament with the loop formed at its distal end. In the third embodiment, a length of suture is inserted through the interior bore of the coil either prior to or after the pointed tip of the coil is penetrated through body tissue to be sutured. After the coil tip has penetrated through the tissue, the length of suture is grasped adjacent the bore opening at the coil distal end. The length of suture is then pulled from the coil interior bore as the coil is retracted from the penetration, thereby leaving the length of suture extending through the penetration as the coil is removed.

The fourth embodiment of the invention is similar to the first described embodiment except that in lieu of the length of filament with the loop at its proximal end, a pointed tip or needle is removably attached to the bore opening at the distal end of the coil. The needle is connected to a length of suture that extends through the bore opening and the interior bore of the coil.

In use, the needle is passed through tissue to be sutured. The needle and a portion of the attached length of suture are then removed from the distal end of the coil with a grasper. The coil is then retracted from the penetration leaving the length of suture in the tissue penetration as the coil is removed. The needle may then be cut free or reused, for example, being manipulated by a grasper or another needle driver in additional suturing of the tissue.

The fifth embodiment of the inventive apparatus is similar to the first and fourth embodiments described earlier. This embodiment also employs a pointed tip removably attached to the bore opening at the distal end of the instrument coil. However, the pointed tip is not attached to a length of suture as in the fourth embodiment, but is attached to a pair of filaments that extend through the interior bore of the coil and through the hollow interior of the handle to a reciprocating mechanism of the type employed with the first embodiment of the apparatus. Manual reciprocation of the mechanism knob causes the pointed tip to be extended out of the bore opening at the distal end of the coil by the pair of filaments and retracted back over the bore opening at the distal end of the coil. The pair of filaments are constructed from shape memory materials that cause the filaments to separate from each other as the pointed tip is extended from the distal end of the coil. The spacing between the pair of filaments enables a length of suture to be passed therethrough. Retracting the filaments back into the coil bore and reattaching the pointed tip on the distal end of the coil securely holds the length of suture proximate to the pointed tip. The instrument may then be employed in suturing tissue in a manner similar to previously described embodiments, either by first attaching the length of suture proximate to the pointed tip prior to penetration of the tip through the tissue, or by first penetrating the tissue with the pointed tip and then extending the tip from the coil distal end to attach the length of suture proximate to the pointed tip prior to retraction of the coil and the attached length of suture back through the tissue penetration.

The sixth embodiment of the invention is the only embodiment that does not require the hollow interior bore extending through the coil. In this embodiment, the coil is a solid member having the pointed tip at its distal end. An aperture extends through the coil adjacent the pointed tip. The aperture is dimensioned sufficiently large to enable a length of suture to be passed through the aperture. Instead of a closed eye aperture, an open eye aperture may also be employed. The open eye aperture has an open side which makes threading of the aperture much easier. This instrument may be employed in suturing tissue in a manner similar to those of previously described embodiments. A length of suture may be inserted through the aperture prior to the pointed tip being penetrated through the tissue to be sutured, or the tip may first be penetrated through the tissue and then a length of suture may be inserted through the aperture prior to retraction of the tip and the length of suture through the tissue penetration.

The seventh embodiment is similar to the sixth except that the handle has an opening at its distal end to permit a surgical instrument to be inserted completely through the handle.

Each of the embodiments of the apparatus of the invention described above provides a surgical instrument that facilitates passing a length of suture through tissue to be sutured in deep incision surgery and particularly in laparoscopic surgery.

BRIEF DESCRIPTION OF THE DRAWINGS

Further objects and features of the present invention are revealed in the following detailed description of the preferred embodiments of the invention and in the drawing figures wherein.

DESCRIPTION OF THE PREFERRED EMBODIMENTS

Figure 1:
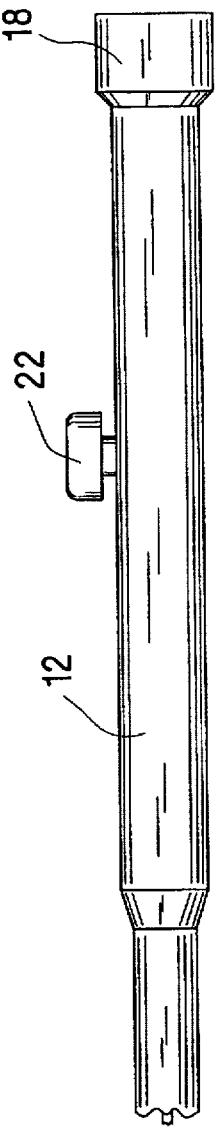
FIG. 1 shows a broken side view of a first embodiment of the surgical instrument of the invention.
Figure 3:
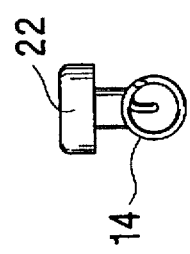
FIG. 3 shows an end view of the instrument of FIG. 1.
Figure 4:
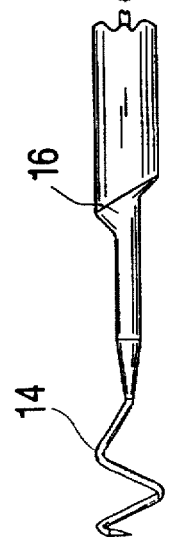
FIG. 4 shows a broken side view of a mechanism employed in extending and retracting a filament loop from the coil distal end of the instrument shown in FIG. 1.

Each of the embodiments of the invention are constructed of materials acceptable for use in surgical instruments. The first embodiment of the suturing instrument of the invention is basically comprised of a handle 12 and a coiled projection 14. As shown in FIG. 1, the handle has a center axis that is coaxial with a center axis around which the coil projection 14 revolves. In variant embodiments, it may be desirable that the handle center axis and the coil projection center axis not be coaxial. Such an embodiment of the invention is discussed later.

Figure 5:
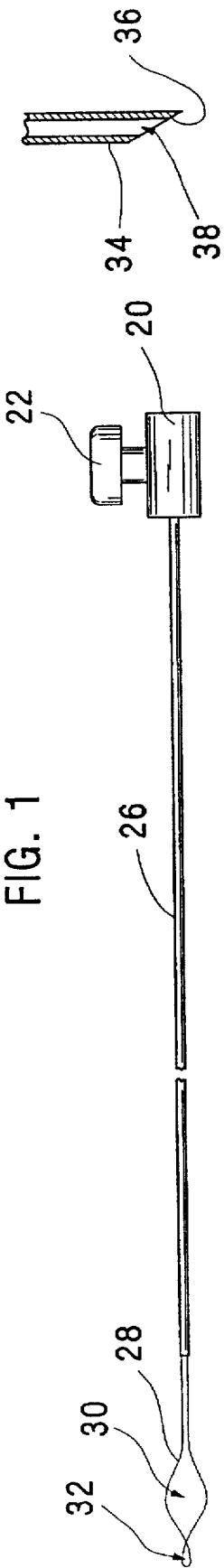
FIG. 5 shows a partial cross section of the pointed coil tip of the instrument of FIG. 1.

The handle 12 has an elongated configuration with opposite distal 16 and proximal 18 ends. The proximal end 18 of the handle may be provided with a Luer fitting or some other type of seal to maintain laparoscopic insufflation pressure. The handle has a hollow interior bore extending through its length. A sliding block 20 is received in the handle bore for sliding, reciprocating movement therein. A manual knob 22 extends laterally from the sliding block 20 through an oblong slot 24 in a side of the handle. Reciprocating movement of the manual knob 22 along the slot 24 reciprocates the sliding block 20 within the handle interior. A narrow rod 26 is connected to the sliding block 20. An opposite end of the rod 26 from the block 20 has a filament loop 28 secured thereto. The filament loop 28 is constructed in a FIG. 8 configuration from elastic materials, plastic materials having elastic properties like polyester, polypropylene, or nylon may be used. The filament loop may also be constructed of metals like stainless steel or super elastic nickel-titanium (Nitinol). In the preferred embodiment, the filament loop 28 is constructed of super elastic Nitinol wire. The loop 28 is formed in a FIG. 8 configuration with a large lobe 30 and a smaller lobe 32 of the FIG. 8 positioned at the distal end of the loop from the rod 26. The coil projection 14 is connected to the handle distal end 16 and, in the preferred embodiment, passes through at least one complete helical revolution around the center axis of the coil as it extends from the handle distal end 16 to the distal end 34 of the coil. In variant embodiments the coil projection 14 may be formed with less than one complete revolution or may be formed with a plurality of revolutions around the coil center axis as it extends from the handle to its distal end. The pointed tip 36 of the coil distal end is shown in more detail in FIG. 5. In FIG. 5 it can be seen that the pointed tip 36 of the coil is pointed like a bevel cut hypodermic needle with a bore opening 38 at the tip. This configuration of the tip enables it to easily penetrate body tissue.

Figure 2:
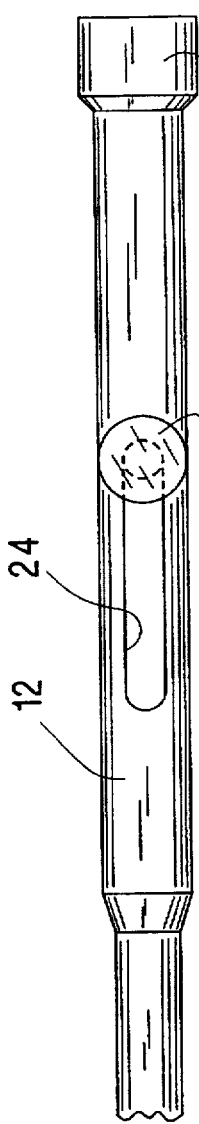
FIG. 2 shows a partial top view of the instrument shown in FIG. 1.
Figure 6:
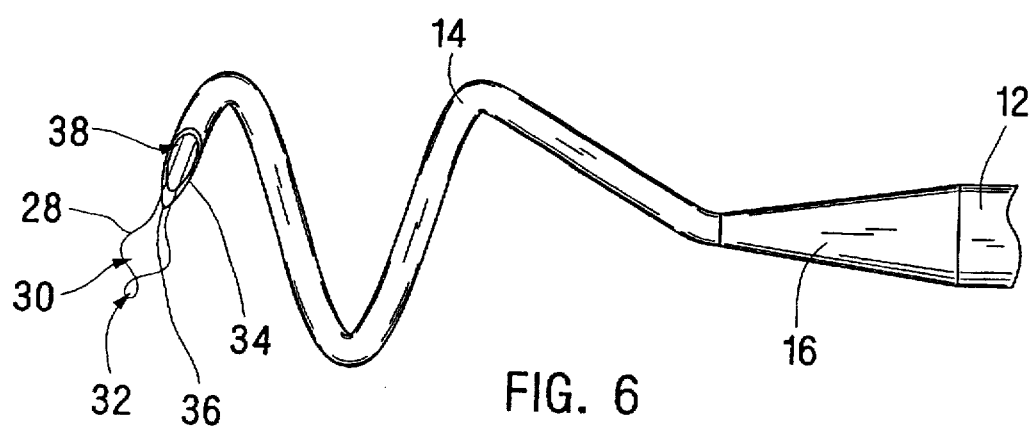
FIG. 6 shows an enlarged view of the coil of the FIG 1 embodiment of the invention.

The coiled projection 14 is formed as a hollow tube with an interior bore extending through the coil as it extends from the handle 12 to the coil distal end 16. The interior bore of the coil exits the coil through the bore opening 38 at the coil's pointed tip. The coil interior bore communicates with the hollow interior of the handle 12. The rod 26 connected to the sliding mechanism block 12 in the handle interior positions the filament loop 38 in the interior bore of the coil 14 adjacent the bore opening 38 with the manual knob 22 in its retracted position shown in FIGS. 1 and 2. Moving the knob distally to its extended position in the slot 24 will cause the filament loop 28 to be extended out of the coil bore through the bore opening 38. The elastic characteristics of the materials employed in constructing the filament loop 28 cause the loop to expand to its FIG. 8 configuration as it is extended from the bore opening 38 as shown in FIG. 6. Moving the manual knob 22 back to its retracted position shown in FIG. 2 again retracts the entire filament loop 28 into the coil interior bore to where it is positioned adjacent the bore opening 38.

In use of the embodiment of the invention shown in FIGS. 1 through 6, the elongated handle 12 of the instrument enables it to be used in positioning the coil distal end 34 adjacent tissue to be sutured in a deep incision, or alternatively to insert the instrument through a canula or trocar in performing laproscopic surgery. With the coil distal end 34 positioned adjacent body tissue to be sutured, the filament loop 28 may then be extended from the bore opening 38 at the coil distal end by manual manipulation of the knob 22 to its forward position on the handle. A length of suture may be inserted through the larger lobe 30 of the filament loop. The loop 28 is then retracted through the bore opening 38 into the coil interior by manipulation of the knob 22 rearward to its retracted position. The movement of the filament loop 28 through the bore opening 38 forces the suture to move from the large loop lobe 30 into the smaller loop lobe 32 at the loop distal end where it is retained.

With the suture securely held to the pointed tip 36 of the coil, the tip may then be passed through tissue to be sutured simultaneously pulling the length of suture through the penetration in the tissue made by the tip. With the pointed tip 36 projecting from the end of the tissue penetration, the knob 22 may then be manipulated to extend the filament loop 28 from the bore opening 38 at the tip. The length of suture passed through the tissue penetration may then be grasped by a surgical grasper and removed from the filament loop 28. The filament loop may then be retracted back into the coil 14 and the coil removed from the tissue penetration leaving the length of suture in the penetration. The length of suture may then be tied or used for subsequent tissue penetration.

As described earlier, the coil projection 14 can be formed with more than one complete helical revolution of the coil. In use of this variant embodiment, the handle 12 may be rotated several times so that the pointed tip 36 of the coil will penetrate and pass through the tissue several times simultaneously pulling the length of suture through the tissue each time the pointed tip is passed through the tissue. In this manner, this first described embodiment of the invention (as well as later described embodiments) may be employed to form a running suture.

In an alternative use of this first embodiment of the invention, the pointed tip 36 of the coil may first be passed through the tissue to be sutured without a length of suture secured thereto. Once passed through the tissue, the knob 22 is manipulated to extend the filament loop 28 from the coil pointed tip. A length of suture is then passed through the filament loop 28 and the loop is retracted into the coil interior by manipulation of the knob 22. The coil is then removed through the tissue penetration pulling the length of suture through the penetration behind it. Once removed from the tissue penetration, the filament loop 28 is then extended from the coil tip 36 and the length of suture removed from the loop. The length of suture passed through the tissue penetration in this manner may then be knotted or manipulated for further purposes.

Figure 7:
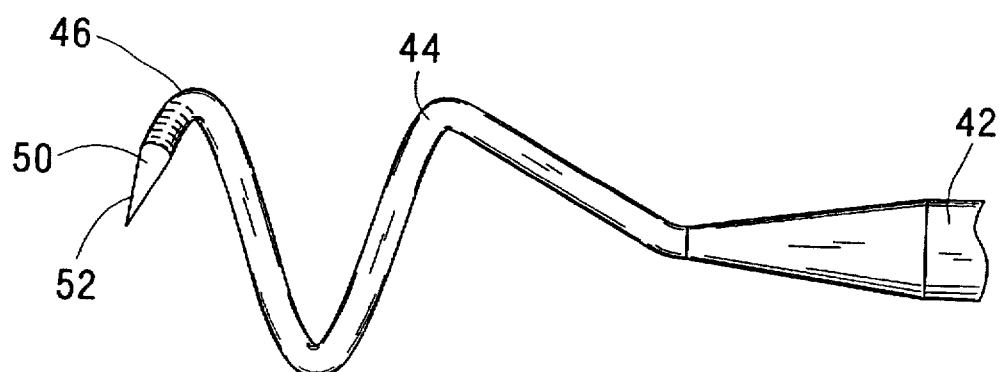
FIG. 7 shows an enlarged view of the coil of a further embodiment of the invention.
Figure 8:
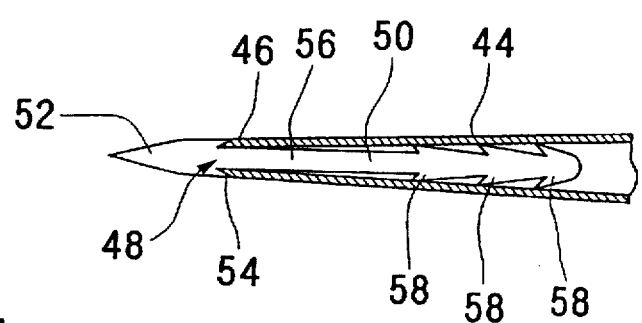
FIG. 8 is a partial view of the distal end of the coil of FIG. 7.

FIGS. 7 and 8 show a further embodiment of the instrument of the invention. This embodiment is similar to the previously described embodiment except that it does not employ the sliding block 20, attached rod 26 and filament loop 28 of the previously described embodiment. The handle 42 and coil projection 44 of the FIGS. 7 and 8 embodiment are substantially identical to that of the previously described embodiment except that, with this embodiment not having the sliding block, the handle does not include the oblong slot 24. Additionally, the distal end 46 of the coiled projection does not have the bevel cut of a hypodermic needle as did the previous embodiment, but has a bore opening 48 in a plane substantially perpendicular to the center axis of the coil interior bore.

Inserted into the bore opening 48 is a fastener member 50. The fastener member 50 is constructed of any material acceptable for use in surgical operations and having limited flexibility. The fastener member is formed with a forward pointed tip 52 having one or more resilient barbs 54 surrounding a rearward end of the tip. A shank 56 extends rearward from the tip 52 to one or a series of barbs 58 formed around the rearward end of the fastener member. The fastener member 50 is inserted into the coil interior bore with the pointed tip 52 projecting from the bore opening 48 as shown in FIG. 7 and 8. Alternatively, the fastener member 50 can be entirely received within the interior bore adjacent the bore opening.

In use of the FIG. 7 and 8 embodiment, as in the previously described embodiment, the pointed tip 52 is first driven through tissue desired to be sutured. The fastener member 50 is penetrated through the tissue until the barb 54 of the pointed tip 52 is within tissue or projects from the opposite side of the tissue penetration. The coil 44 is then retracted through the tissue penetration causing the fastener member 50 to be simultaneously withdrawn from the coil interior bore through the bore opening 48. If necessary, the tissue being sutured can be held in close proximity as the coil is withdrawn to ensure that the coil is completely drawn from the penetration through the tissue before the series of barbs 58 at the rearward end of the fastener member 50 are withdrawn from the bore interior. Withdrawing the coil 44 from the tissue penetration leaving the fastener member 50 in its place completes proximation of the tissue. Alternatively, an election means can be provided to eject the fastener when desired. The tip barb 54 at the forward end of the fastener member 50 and the series of barbs 58 at the rearward end of the member project from the tissue at opposite ends of the coil penetration and securely hold the tissue.

Figure 9:
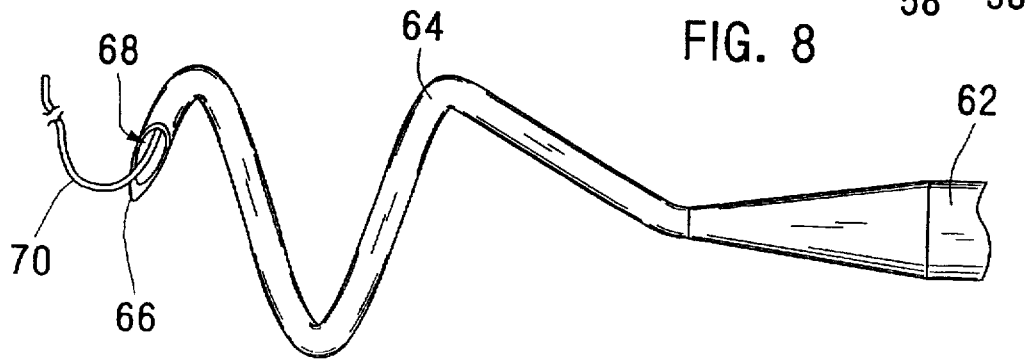
FIG. 9 is an enlarged view of the coil of a further embodiment of the invention.

FIG. 9 shows a further embodiment of the inventive instrument employing a handle 62 and coiled projection 64 substantially identical to that of the first described embodiment except that it does not employ the sliding block 20, rod 26, and filament loop 28 of the first embodiment. Furthermore, because the sliding block mechanism is not employed, the handle does not have the oblong slot of the first embodiment.

In the embodiment of FIG. 9, the distal end of the coiled projection 64 from the handle 62 is again formed with a pointed tip 66 like that of a bevel cut hypodermic needle. The interior bore of the coil projection 64 again communicates with the hollow interior of the handle 62 and exits the coil projection through a bore opening 68 at the pointed tip 66.

In use of this embodiment, a length of suture materials 70 is inserted through the coiled projection interior bore and into the hollow interior of the handle with only a small portion of the suture material projecting out of the bore opening 68. The suture loading through the bore may occur within or without the patient's body. The pointed tip 66 of the coil is penetrated through the tissue to be sutured until it emerges from the tissue at the opposite end of the penetration. The length of suture projecting out from the bore opening 68 may then be held by a separate surgical grasper and the coil projection 64 is retracted back through the tissue penetration, leaving the length of suture 70 in its place in the penetration. With the coil 64 removed from the penetration, the portion of the suture left in the penetration may then be cut free from the suture remaining in the coil bore. The cut piece of suture is then knotted to complete the suture or used otherwise.

Alternatively, the instrument of FIG. 9 may be employed in penetrating the tissue to be sutured without previously inserting suture into the coil interior bore. With the pointed tip 66 of the instrument projecting from the tissue at the opposite end of the penetration, a length of suture may then be drawn into the coil interior bore through the bore opening 68 by a source of vacuum communicating with the proximal end of the handle 62. The vacuum draws the length of suture into the bore interior through the bore opening 68. The distal end of the suture is held with a grasper to prevent the entire length of suture being drawn into the coil interior. The coil projection 64 is then withdrawn from the tissue penetration leaving the length of suture in the penetration. The portion of suture left in the tissue penetration is then cut and knotted to complete the ligature in the same manner as the previously described embodiment.

Figure 10:
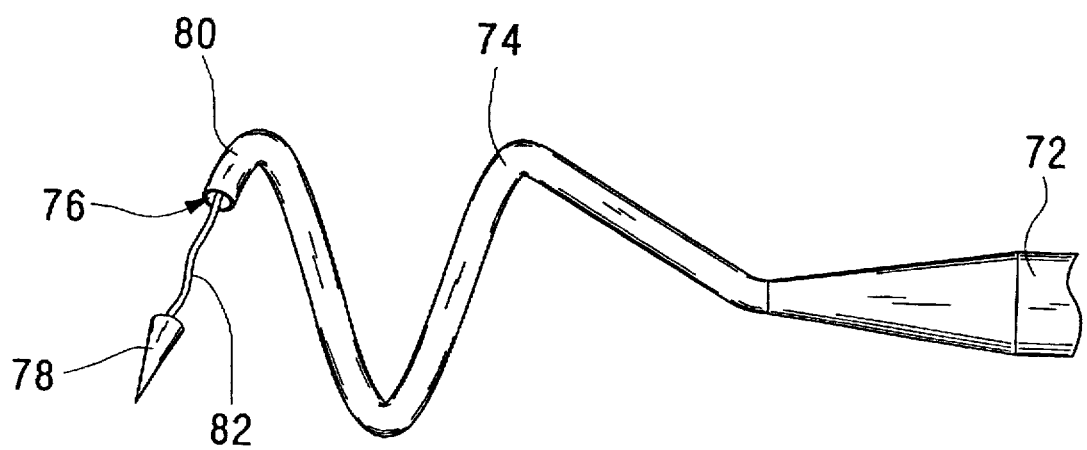
FIG. 10 is an enlarged view of the coil of a further embodiment of the invention.

The FIG. 10 embodiment of the instrument employs a handle 72 and a coiled projection 74 substantially identical to that of the FIG. 7 and 8 embodiment. This embodiment has a bore opening 76 at the distal end of the coiled projection 74 positioned in a plane substantially perpendicular to the center axis of the coil interior bore. The pointed tip of the coil is provided by a needle 78 that is removably attached to the coiled projection distal end 80. The rearward end of the needle 78 opposite its point may be configured to be received inside the bore opening 76 of the coil. In such a configuration a stop would be provided in the coil interior to prevent the needle from passing entirely through the bore opening 76 into the bore. Alternatively, the needle 78 could be provided with a rearward barb such as the tip barb 54 of the FIG. 7 and 8 embodiment to prevent the needle from passing entirely into the coil interior bore.

A length of suture 82 is connected to the rearward end of the needle 78 and then passes through the bore opening 76 and the interior bore of a coil 74. The length of suture may pass entirely through the handle 72 and be held by a tensioning apparatus at the proximal end of the handle (not shown) or alternatively held by the surgeon to maintain tension on the suture.

In use of the embodiment of FIG 10, the pointed tip of the needle 78 and the coiled projection 74 are passed through the tissue to be proximated until the needle 78 is exposed on the opposite side the tissue penetration. The needle 78 is then grasped by a surgical grasper and pulled from the coil distal end 80 causing a length of suture to be pulled from the coil. With the grasper holding the needle 78, the coil projection 74 is then removed from the tissue penetration leaving a portion of the suture 82 in its place in the penetration. With the coiled projection 74 completely removed from the tissue penetration, the needle 78 may be cut from the suture and the end of the suture projecting from the coil bore opening 76 may be cut to enable the suture to be tied completing the stitch.

Figure 11:
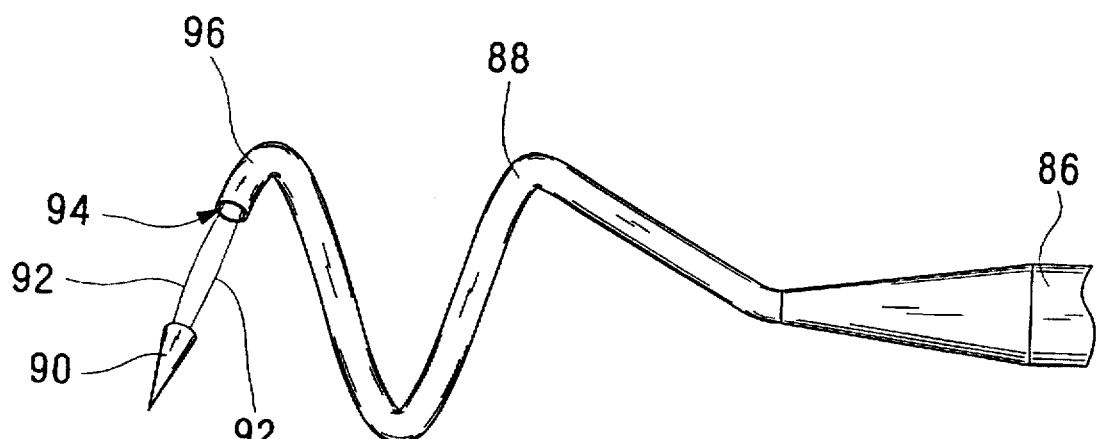
FIG. 11 is an enlarged view of the coil of a further embodiment of the invention.

The embodiment of the invention shown in FIG. 11 is similar to the FIG. 10 embodiment in that it also employs a handle 86, a coiled projection 88, and a pointed tip in the form of a needle 90, the construction of which is substantially identical to that of the previously described embodiment. The FIG. 11 embodiment differs from the FIG. 10 embodiment in that a length of suture is not attached to the needle 90. Instead, a pair of filaments 92 are attached to the rearward end of the needle 90 and pass through the coiled portion bore opening 94 and the interior bore of the coil to the end of a rod (not shown) substantially identical to that shown in FIG. 4. The rod is part of a manual reciprocating mechanism substantially identical to that of the first described embodiment of the invention. When the knob (not shown) of the mechanism is moved to its forward, extended position, the pair of filaments are pushed by the mechanism rod through the coil interior and out through the bore opening 94 extending the needle 90 from the distal end of the coiled projection as shown in FIG. 11. Movement of the knob (not shown) of the reciprocating mechanism back to its rearward, retracted position causes the rod of the mechanism to pull the pair of filaments 92 back through the coil interior bore causing the needle 90 to reattach itself to the coil distal end 96.

In use of the instrument of FIG. 11, the reciprocating mechanism may first be actuated to extend the pair of filaments 92 and attached needle 90 from the distal end 96 of the coil as shown in FIG. 11. In the preferred embodiment, the pair of filaments 92 are constructed of a material having elastic characteristics such as those materials described earlier with reference to the FIG. 6 embodiment of the invention. With a pair of filaments 92 extended from the distal end 96 of a coil, they bow away from each other providing a void between the filaments for insertion of a length of suture. The suture is inserted between the pair of filaments 92 and the mechanism is retracted to its rearward position causing the filaments 92 to be retracted back into the bore interior and causing the needle 90 to reattach to the coil distal end 96, thereby securing the length of suture to the distal end of the coil. The instrument is then used to penetrate the body tissue to be sutured passing the needle 90 through the tissue until it is exposed on the opposite side of a tissue penetration. The mechanism may then be operated moving the knob to its forward position and thereby extending the needle 90 and the pair of filaments 92 from the bore opening 94 at the coil distal end 96. The length of suture may then be removed from between the pair of filaments 92 and the filaments retracted into the bore reattaching the needle 90 to the coil distal end 96. Grasping the suture, the coil and attached needle may then be removed from the tissue penetration leaving the length of suture in place in the penetration. With the coil and needle removed from the tissue, the suture may then be knotted to complete the suture.

Alternatively, the needle 90 may be penetrated through the tissue to be sutured prior to suture material being secured to the coil distal end. With the needle exposed at the opposite end of the tissue penetration, the manual mechanism is then reciprocated to cause the needle and pair of filaments 92 to be extended from the bore opening 94 at the coil distal end 96. A length of suture is then inserted between the pair of filaments 92 and the reciprocating mechanism activated to retract the pair of filaments 92 back into the coil interior reattaching the needle 90 to the coil distal end 96 and securely holding the suture to the coil distal end. The coil and needle are then retracted out of the tissue penetration pulling the length of suture through the penetration. With the coil and needle completely removed from the tissue penetration, the manual mechanism is activated to extend the needle and pair of filaments from the coil distal end enabling the suture to be removed from between the filaments. The length of suture pulled through the tissue penetration may then be knotted to complete the suture.

Figure 12:
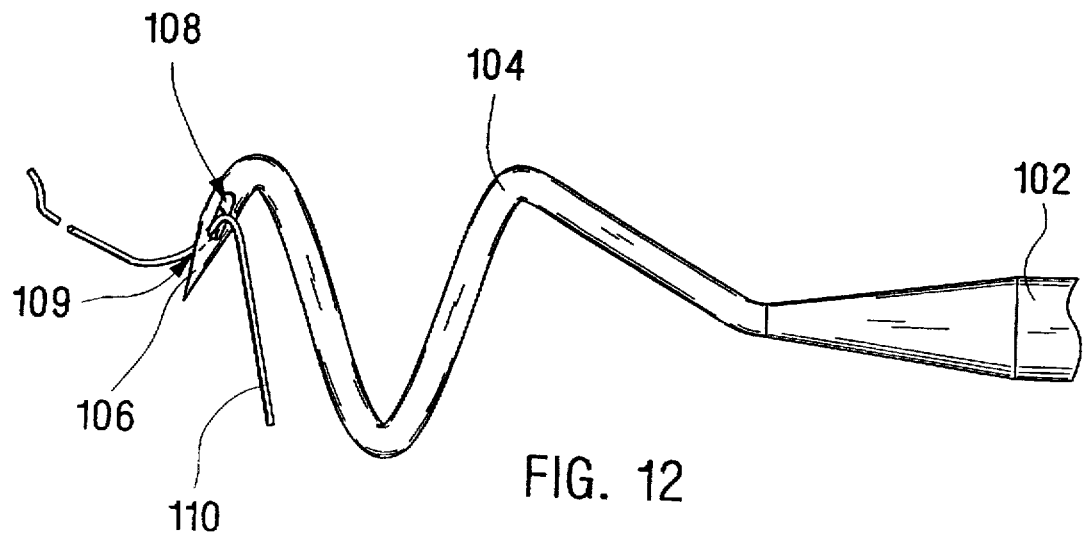
FIG. 12 is an enlarged view of the coil of a further embodiment of the invention.

FIG. 12 shows a further embodiment of the instrument of instrument of the invention. The FIG. 12 embodiment, as with previous embodiments, employs a handle 102 and a coiled projection 104 having a pointed tip 106. However, in this embodiment, the handle 102 and coiled projection 104 are not hollow. An aperture 108 extends transversely through the pointed tip 106. The aperture 108 is a closed eye dimensioned sufficiently large to enable passing a length of suture through the aperture. Alternatively, instead of the closed eye aperture, an open eye aperture may be employed. The open eye aperture has an open side which makes threading of the aperture much easier. The open side of an open eye aperture is represented by the dashed lines 109 in FIG. 12.

In use of this embodiment of the invention, a length of suture may be inserted through the aperture 108 prior to penetration of body tissue to be sutured. With the suture 110 inserted through the aperture 108, the pointed tip 106 is then penetrated through body tissue until the aperture is completely exposed on the opposite side of the tissue penetration. The length of suture 110 may then be grasped by a surgical grasper and removed from the aperture. The pointed tip 106 is then removed from the tissue penetration leaving the length of suture in place in the penetration. With the tip 106 completely removed from the tissue, the suture may then be knotted to complete the suture.

Alternatively, the FIG. 12 embodiment may first be penetrated through the tissue to be sutured prior to the length of suture being attached to the pointed tip. The pointed tip 106 is first penetrated through the tissue until the aperture 108 of the tip is exposed at the opposite end of the tissue penetration. A length of suture is then inserted through the aperture 108. The pointed tip 106 is then removed from the tissue penetration pulling the length of suture through the penetration. Once the pointed tip 106 is completely removed from the tissue, the suture is removed from the aperture 108 and knotted completing the suture.

Figure 13:
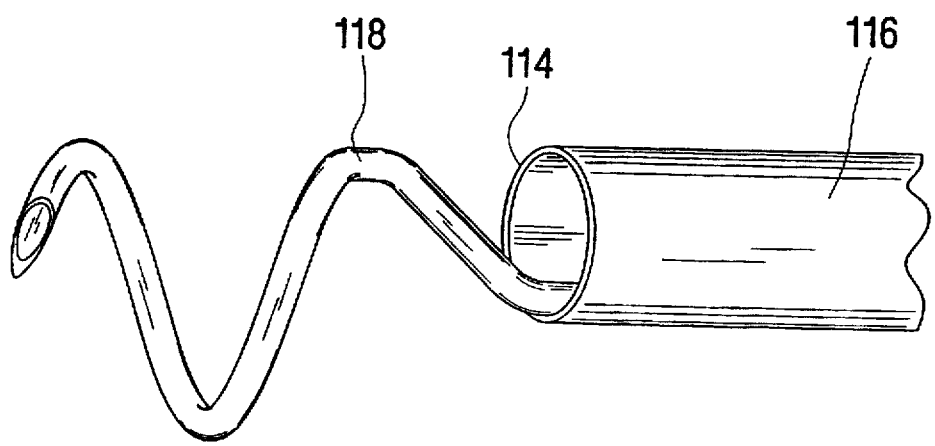
FIG. 13 is an enlarged view of the coil of a further embodiment of the invention.

FIG. 13 shows a still further embodiment of the invention. The FIG. 13 embodiment is substantially identical to that of FIG. 12 except that the distal end 114 of the handle 116 is not closed on the coiled projection 118 but is left open. This open hollow bore completely through the handle 116 enables additional surgical instruments to be inserted through the handle interior for use in association with the coiled projection 118. The center axis of the handle interior bore is coaxial with the center axis of the revolutions of the coiled projection 118 enabling a surgical instrument, such as a surgical grasper, to be inserted through the interior of the handle 116 and through the interior of the revolutions of the coiled projection 118. Although the handle with the open proximal end 116 is shown used with the coiled projection 118 of the type disclosed earlier with reference to the FIG. 12 embodiment, it should be understood that a handle having an open distal end such as that shown in FIG. 13 may be employed with the coiled projections of the other previously described embodiments of the invention. As in all of the embodiments, the proximal end may be fitted with a seal to maintain laparoscopic insufflation pressure.

While the present invention has been described by reference to specific embodiments, it should be understood that modifications and variations of the invention may be constructed without departing from the scope of the invention defined in the following claims.

What is claimed is:

1. A surgical suturing instrument comprising:
   an elongate handle having opposite proximal and distal ends;
   a projecting coil on the distal end of the handle, the projecting coil extending from the handle distal end through a curve of the coil to a pointed tip of the coil, the pointed tip and curve being configured to enable penetration of the pointed tip through body tissue and passage of the coil through the penetration, and
   the coil pointed tip is removable from the coil and is removably received on a distal end of the coil, whereby the pointed tip can be passed through a tissue by penetrating the tissue with the coil pointed tip and passing the coil through the penetration, and then removing the pointed tip from the coil distal end as the coil is removed from the penetration of the tissue leaving the pointed tip in the penetration as the coil is removed.

2. The instrument of claim 1, wherein:
   the coil distal end has a bore opening therein, the pointed tip has opposite forward and rearward ends and the rearward end of the pointed tip is received in the coil bore opening in removably receiving the pointed tip on the distal end of the coil.

3. The instrument of claim 2, wherein:
   the rearward end of the pointed tip has at least one barb thereon and the forward end of the pointed tip has at least one barb thereon, and together the barbs hold the pointed tip in the tissue penetration.

4. The instrument of claim 2, wherein:
   the bore opening has a center axis and the bore opening is positioned in a plane that is perpendicular to the bore opening center axis.

5. The instrument of claim 1, wherein:

the coil has a center axis around which the curve extends, and the pointed tip and curve are configured to enable penetration of the pointed tip through tissue and passage of the coil through the penetration by rotating the coil about its center axis.

6. The instrument of claim 1, wherein:

the curve of the coil is generally helical and extends through at least one complete revolution at its extends from the handle distal end to the pointed tip of the coil.

7. The instrument of claim 1, wherein:

the coil distal end has a bore opening therein, the pointed tip has opposite forward and rearward ends, a barb is provided on the tip rearward end and the barb engages against the coil distal end and resists passage of the tip through the bore opening.

8. The instrument of claim 7, wherein:

a shank projects from the rearward end of the pointed tip and is received through the bore opening.

9. The instrument of claim 8, wherein:

the barb on the tip rearward end is directed rearwardly toward the shank and the shank has a second barb that is directed forwardly toward the pointed tip.

10. The instrument of claim 8, wherein:

the barb on the tip rearward end is directed rearwardly toward the shank and a series of barbs are provided on the shank and each barb of the series of barbs is directed forwardly toward the pointed tip.

11. The instrument of claim 8, wherein:

the coil has an interior bore that exits the coil through the bore opening and the shank is contained in the coil interior bore with the pointed tip received on the distal end of the coil.

12. A method of inserting a fastener into body tissue using an instrument having an elongate handle with a center axis and opposite distal and proximal ends, and having a helically curved projection at the handle distal end that curves around an axis of the projection parallel to the handle axis to a distal end of the projection, the projection having an interior bore that exits the projection through a bore opening at the distal end of the projection, the method comprising:

inserting a fastener having a pointed tip and a shank extending rearwardly from the tip into the projection interior bore by inserting the shank through the bore opening and into the projection interior bore until only the fastener tip projects from the bore;

penetrating the body tissue with the pointed tip by rotating the handle in a first direction about its center axis;

passing the projection and the pointed tip through the tissue penetrated by the projection tip; and, retracting the projection and removing the shank from the projection interior bore leaving the shank in the tissue penetrated by rotating the handle in a second direction about its center axis.

13. The method of claim 12, wherein:

the fastener has a barb at a rearward end of the pointed tip and the step of removing the fastener shank from the projection includes rotating the handle in the second direction causing the pointed tip barb to engage the tissue penetrated by the fastener and thereby holding the fastener in the tissue penetration as the projection is removed from the penetration.

14. The method of claim 13, wherein:

the fastener has a series of barbs on the shank and the step of removing the fastener shank from the projection includes rotating the handle in the second direction and leaving a portion of the shank in the tissue penetrated and removing the projection from at least a portion of the shank outside the tissue penetrated.

* * * * *